(12) United States Patent
Zuniga et al.

(10) Patent No.: US 9,638,616 B2
(45) Date of Patent: May 2, 2017

(54) DEVICES AND METHODS FOR GRAVIMETRIC SENSING IN LIQUID ENVIRONMENTS

(75) Inventors: Chiara Zuniga, Boston, MA (US);
Matteo Rinaldi, Boston, MA (US);
Gianluca Piazza, Pittsburgh, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1037 days.

(21) Appl. No.: 13/882,611

(22) PCT Filed: Nov. 1, 2011

(86) PCT No.: PCT/US2011/058712
§ 371 (c)(1),
(2), (4) Date: Aug. 29, 2013

(87) PCT Pub. No.: WO2012/061338
PCT Pub. Date: May 10, 2012

(65) Prior Publication Data
US 2013/0330835 A1    Dec. 12, 2013

Related U.S. Application Data

(60) Provisional application No. 61/408,847, filed on Nov. 1, 2010.

(51) Int. Cl.
*G01N 33/551* (2006.01)
*G01N 9/00* (2006.01)
(Continued)

(52) U.S. Cl.
CPC .............. *G01N 9/002* (2013.01); *G01N 5/02* (2013.01); *G01N 29/022* (2013.01);
(Continued)

(58) Field of Classification Search
None
See application file for complete search history.

(56) References Cited

U.S. PATENT DOCUMENTS

| | | |
|---|---|---|
| 2008/0085212 A1 | 4/2008 | Adams et al. |
| 2008/0247264 A1 | 10/2008 | Gabl et al. |
| 2010/0216172 A1 | 8/2010 | Shih et al. |

OTHER PUBLICATIONS

Fang et al, "Metal-Organic Thin-Film Encapsulation for MEMs", Journal of Micromechanics and Microengineering, vol. 18, No. 10, Aug. 26, 2008, pp. 1-8.*

(Continued)

*Primary Examiner* — Chris L Chin
(74) *Attorney, Agent, or Firm* — RatnerPrestia (57) ABSTRACT

Devices and methods for gravimetric sensing are disclosed. A gravimetric sensor includes a piezoelectric resonator and an encapsulating layer formed on the surface of the resonator. The encapsulating layer defines a channel within the encapsulating layer on the surface of the resonator. The sensor is fabricated by forming a piezoelectric resonator, forming a sacrificial layer on a surface of the piezoelectric resonator, forming an encapsulating layer over the sacrificial layer on the resonator, and etching the sacrificial layer to remove the sacrificial layer and form a channel on the surface of the resonator. The sensor is used by supplying the liquid to the channel of the gravimetric sensor, operating the piezoelectric resonator, detecting a change in a resonant frequency of the resonator, and determining a presence of the analyte in the liquid from the change in resonant frequency of the resonator.

12 Claims, 6 Drawing Sheets

(51) Int. Cl.
*G01N 29/02* (2006.01)
*G01N 5/02* (2006.01)
*G01N 29/036* (2006.01)

(52) U.S. Cl.
CPC ... *G01N 29/036* (2013.01); *G01N 2291/0255* (2013.01); *G01N 2291/0256* (2013.01); *G01N 2291/0427* (2013.01)

(56) References Cited

OTHER PUBLICATIONS

International Search Report dated Mar. 1, 2012, application No. PCT/US11/58712.
Fang, et al., Metal-Organic Thin-Film Encapsulation for MEMS. J. Micromech. Microeng., vol. 18, No. 10, Aug. 26, 2008, pp. 1-8.

* cited by examiner

| Table 1 | | $f_0$ [MHz] | Q | $k^2 \cdot Q$ |
|---|---|---|---|---|
| 278 MHz PRN | air | 278.2 | 383 | 2.6 |
| | water | 277.6 | 210 | 1.6 |
| | 25% glycerol | 276.7 | 180 | 1.6 |
| 458 MHz PRN | air | 458 | 1090 | 9.1 |
| | water | 456.2 | 182 | 1.5 |
| | 25% glycerol | 455.6 | 111 | 1 |
| 458 MHz CMR | air | 460.7 | 961 | 9.3 |
| | water | 458.6 | 90 | 0.26 |

SUMMARY OF EXPERIMENTAL RESULTS

FIG. 4

| FEM Simulations | CMR | CMR w/ top AlN | PNR-S |
|---|---|---|---|
| $C_0$ – Geometrical | 244 fF | 267 fF | 260 fF |
| $C_p$ – Parasitic in $H_2O$ | 682 fF | 173 fF | 38 fF |
| $C_{tot}$ – Total capacitance in $H_2O$ | 926 fF | 440 fF | 298 fF |
| Energy density stored in device | 1.01 nJ/m·V$^2$ | 1.01 nJ/m·V$^2$ | 1.04 nJ/m·V$^2$ |
| Energy density dissipated in $H_2O$ | 1.74 nJ/m·V$^2$ | 0.67 nJ/m·V$^2$ | 0.174 nJ/m·V$^2$ |

FIG. 5

DEVICES AND METHODS FOR GRAVIMETRIC SENSING IN LIQUID ENVIRONMENTS

CROSS-REFERENCE TO RELATED APPLICATIONS

This application is the U.S. National Phase application of PCT International Application No. PCT/US2011/058712, filed Nov. 1, 2011, and claims priority to provisional application Ser. No. 61/408,847, filed Nov. 1, 2010, which applications are incorporated herein by reference in their entireties and for all purposes.

FIELD OF THE INVENTION

The present invention relates to gravimetric sensing, and more particularly, gravimetric sensing applications in liquid environments.

BACKGROUND OF THE INVENTION

In recent years, it has become desirable to use micromechanical devices for high performance gravimetric sensing. In particular, there is demand for miniature sensors for use in the detection of concentrations of potentially harmful and other chemicals. Micromechanical piezoelectric resonators are amenable for use in such sensing applications given their ability to be miniaturized and comparatively high operating frequencies.

Certain applications may require the use of gravimetric sensors in a liquid environment. In these applications, the liquid may generate a viscous force on the sensor, which limits its effectiveness. Thus, there is an omnipresent need for improved gravimetric sensors designed to function in a liquid environment

SUMMARY OF THE INVENTION

Aspects of the present invention are directed to devices and methods for gravimetric sensing.

In accordance with one aspect of the present invention, a gravimetric sensor is disclosed. The gravimetric sensor comprises a piezoelectric resonator having a surface, and an encapsulating layer formed on the surface of the resonator. The encapsulating layer defines a channel within the encapsulating layer on the surface of the resonator.

In accordance with another aspect of the present invention, a method for fabricating a gravimetric sensor is disclosed. The method comprises forming a piezoelectric resonator, forming a sacrificial layer on a surface of the piezoelectric resonator, forming an encapsulating layer over the sacrificial layer on the resonator, and etching the sacrificial layer to remove the sacrificial layer and form a channel on the surface of the resonator.

In accordance with yet another aspect of the present invention, a method of using a gravimetric sensor to detect an analyte in a liquid is disclosed. The method comprises supplying the liquid to the channel of the gravimetric sensor, operating the piezoelectric resonator, detecting a change in a resonant frequency of the resonator, and determining a presence of the analyte in the liquid from the change in resonant frequency of the resonator.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The exemplary devices and methods described herein relate to gravimetric sensors that incorporate piezoelectric resonators for use in liquid environments, and methods of using and fabricating such sensors. The disclosed sensors are particular suitable to detect trace amounts of a desired analyte in small liquid samples and to detect the density of the liquid inside the sensor (i.e., in the nanochannel).

The disclosed devices and methods generally relate to a new class of devices that comprise a piezoelectric resonant nanochannel adapted to confine a liquid sample within the body of the resonant device. The size and structure of the disclosed devices effectively result in a resonant nanochannel that vibrates laterally (or transversely) along substantially its entire length. Additionally, the resonant nanochannels may be sized to achieve a reduction in sample size necessary for testing (e.g., the volume of the channel may be less than approximately 50 pL, depending on the channel thickness).

The resonant nanochannels of the present invention confine the liquid under test to thicknesses that approach the penetration depth of the acoustic waves generated by the resonator, thereby achieving reduced viscous damping These nanochannels may be configured to maximize the sample-device interaction by delivering the fluid solely on the active sensing surface of the resonant device.

The above-described nanochannel represents an efficient method for the delivery of the bio-sample onto the resonator, and is therefore important in determining the overall performance of a resonant bio-sensor. For example, if the resonator were to be immersed in a large volume of the fluid sample, it would not be statistically able to interact with some of the very low concentration analytes contained in the sample itself, due to viscous damping of the resonator by the liquid sample. Therefore, a major fraction of the analyte could be exhausted without contributing to the detection process.

To the contrary, the exemplary devices described herein permit the efficient delivery of ultra-low concentrations of fluid samples directly on the surface of the sensor.

Figure 1A:
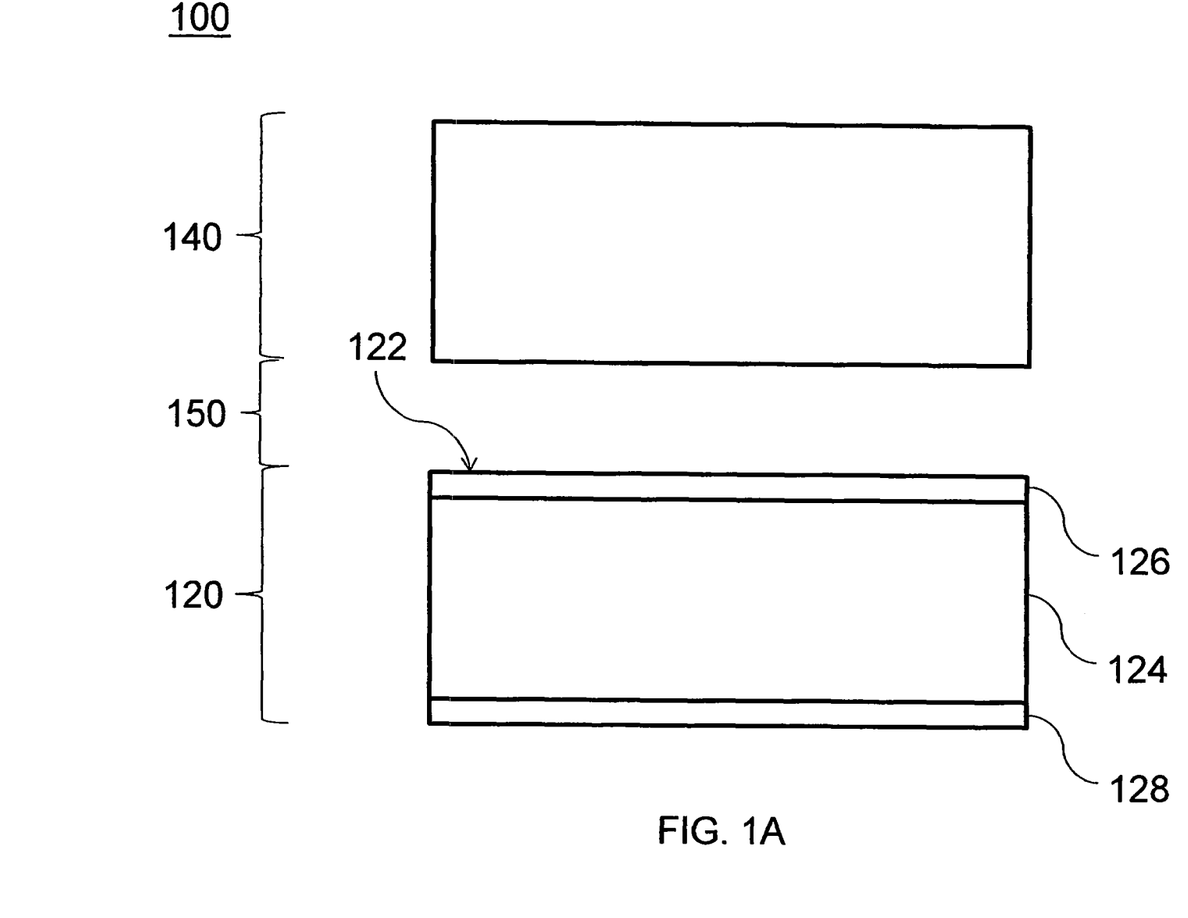
FIG. 1A is a diagram illustrating a cross-sectional side view of an exemplary gravimetric sensor in accordance with aspects of the present invention.
Figure 1B:
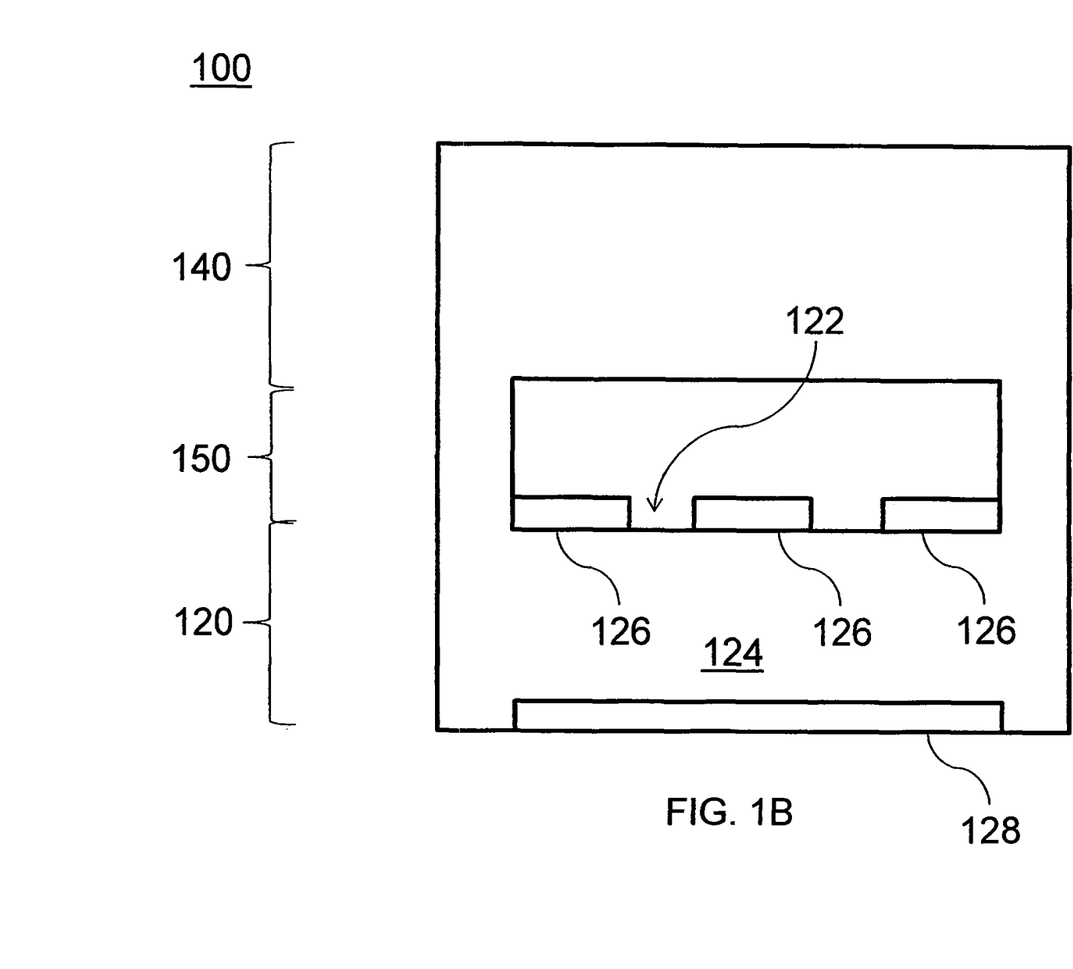
FIG. 1B is a diagram illustrating a cross-sectional end view of an exemplary gravimetric sensor in accordance with aspects of the present invention.

Referring now to the drawings, FIGS. 1A and 1B illustrate an exemplary gravimetric sensor 100 in accordance with aspects of the present invention. Sensor 100 is configured to detect the amount of a desired analyte in a liquid. As a general overview, sensor 100 comprises a piezoelectric resonator 120, an encapsulating layer 140, and a nanochannel 150. Additional details of sensor 100 are provided herein.

Piezoelectric resonator 120 forms the base of sensor 100. Piezoelectric resonator 120 has a surface 122 which defines part of a resonant nanochannel 150 of sensor 100. Piezoelectric resonator 120 is configured to resonate or vibrate under an applied voltage differential, as will be further described below.

Desirably, piezoelectric resonator 120 is a contour-mode piezoelectric resonator, i.e., resonator 120 vibrates in a direction parallel to the plane of the resonator 120. More desirably, piezoelectric resonator 120 vibrates in a direction lateral or transverse to the direction in which resonator 120 (and nanochannel 150) extends. In a preferred embodiment, piezoelectric resonator 120 has a cantilevered shape relative to a substrate (not shown) on which resonator 120 is mounted. Surface 122 for defining nanochannel 150 comprises the upper surface of the cantilevered resonator 120.

Each piezoelectric resonator 120 has a resonant frequency before it is exposed to a liquid sample. The resonant frequency is dependent on the dimensions of the resonator and the mass of the system, as will be understood by one of ordinary skill in the art from the description herein. The exposure of the resonator 120 to the analyte changes the mass of resonator 120. Accordingly, resonator 120 will have a different resonant frequency after it is exposed to the liquid sample containing the analyte.

In an exemplary embodiment, piezoelectric resonator 120 comprises a piezoelectric material layer 124 sandwiched between at least one upper electrode 126 and at least one lower electrode 128. In a preferred embodiment, piezoelectric material layer 124 comprises a layer of aluminum nitride. However, other suitable piezoelectric materials for use as piezoelectric material layer 124 include, for example, zinc oxide, lead zirconate titanate (PZT), gallium arsenide, aluminum gallium arsenide, or any combination thereof. The material and dimensions of piezoelectric material layer 124 are selected such that layer 124 deforms (i.e., expands or contracts) in a particular manner in response to receiving a voltage differential between upper electrode 126 and lower electrode 128. Application of a voltage differential may desirably cause piezoelectric material layer 124 to vibrate in a lateral or transverse direction relative to the direction in which piezoelectric material layer 124 extends (i.e., vibrate into and out of the page in FIG. 1A, or left-right in FIG. 1B). Although piezoelectric resonator 120 is illustrated as comprising a single piezoelectric material layer 124, it will be understood by one of ordinary skill in the art that piezoelectric resonator 120 may include multiple piezoelectric material layers.

Upper electrode 126 and lower electrode 128 are formed on the upper and lower surfaces of piezoelectric material layer 124, as illustrated in FIG. 1A. Electrodes 126 and 128 may be coupled to an external voltage source (not shown) to apply a voltage differential across piezoelectric material layer 124. Suitable voltage sources will be known to one of ordinary skill in the art from the description herein. In an exemplary embodiment, electrodes 126 and 128 comprise layers of conductive material such as, for example, platinum. Other suitable materials for electrodes 126 and 128 may include, but are not limited to, gold, iridium, ruthenium, molybdenum, titanium, rhodium, tungsten, copper, chromium, aluminum, or any combination thereof. It is understood that any conductive material may be used for electrodes 126 and 128, provided that the conductive material satisfies desired material compatibility with piezoelectric material layer 124 (e.g., adhesion, formation of deleterious phases with piezoelectric material layer 124, or a quality of piezoelectric material that may be deposited thereto).

As shown in FIG. 1B, surface 122 of piezoelectric resonator 120 comprises portions of the upper surface of piezoelectric material 124 and the surface of upper electrode 126. However, the location of surface 122 in FIG. 1B is for the purposes of illustration, and is not intended to be limiting. It is desirable to maximize the area of surface 122, in order to maximize the contact between the liquid to be analyzed and the vibrating surface of piezoelectric resonator 120.

Encapsulating layer 140 is formed on surface 122 of piezoelectric resonator 120. Encapsulating layer 140 defines resonant channel 150 within encapsulating layer 140 on surface 122 of resonator 120. Accordingly, encapsulating layer 140 covers at least a portion of, and preferably all of, surface 122 of resonator 120. The shape and size of encapsulating layer 140 may be selected based on the desired position and dimensions of nanochannel 150. In an exemplary embodiment, encapsulating layer 140 comprises a layer of aluminum nitride. However, encapsulating layer 140 may be formed from any of the materials described above with respect to piezoelectric material layer 124.

Nanochannel 150 is defined between the upper surface 122 of piezoelectric resonator 120 and the lower surface of encapsulating layer 140. When resonator 120 has an elongated shape (e.g., is a cantilevered resonator), nanochannel 150 extends along the length of resonator 120 (i.e., left-right in FIG. 1A, and into and out of the page in FIG. 1B). Preferably, nanochannel 150 is defined such that an entire length of nanochannel 150 is adjacent resonator 120, so that the entire length of nanochannel 150 vibrates with piezoelectric resonator 120 when resonator 120 is operated. To this end, it is desirable to maximize the surface area of nanochannel 150 that contacts surface 122 of piezoelectric resonator 120, in order to maximize the sensitivity of sensor 100 to the analyte in the liquid sample. Further, it may be desirable to limit the overall volume of nanochannel 150, in order to enable the use of smaller liquid samples for testing by sensor 100. In an exemplary embodiment, nanochannel 150 has a volume of less than approximately 50 pL.

It will be understood that gravimetric sensor 100 is not limited to the above-described components, but may include additional components, as would be understood by one of ordinary skill in the art from the description herein.

For example, it may be desirable that resonator 120 include a functionalization layer tailored to the analyte to be detected by sensor 100. The functionalization layer may be affixed to surface 122 of resonator 120, with at least a portion of the functionalization layer positioned within nanochannel 150. The functionalization layer is configured to bind with the analyte that is desired to be detected. In one embodiment, this binding may comprise adsorption by the functionalization layer of the analyte. In another embodiment, this binding may comprise reacting with the analyte. In an exemplary embodiment, the functionalization layer comprises a layer of gold. Other suitable materials include platinum, silicon, or chemical and bio-interactive materials (such as polymers, proteins, and/or antibodies). Still other suitable materials for the functionalization layer will be known to one of ordinary skill in the art from the description herein.

Figure 2:
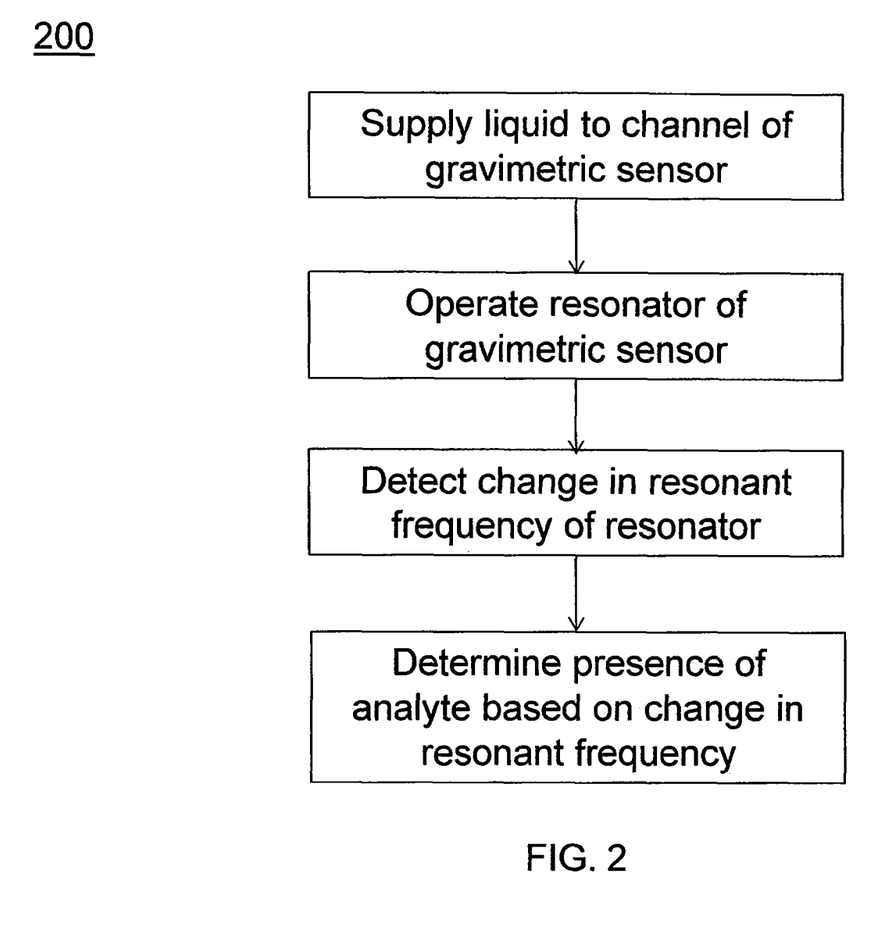
FIG. 2 is a flowchart illustrating an exemplary method for using a gravimetric sensor in accordance with aspects of the present invention.

FIG. 2 is a flow chart illustrating an exemplary method 200 for using a gravimetric sensor in accordance with an aspect of the invention. Method 200 may be used to detect the amount of a desired analyte in a liquid. As a general overview, method 200 comprises supplying liquid to a channel of a sensor, operating a resonator of the sensor, detecting a change in resonant frequency of the resonator, and determining a presence of the analyte. Additional details of method 200 are provided herein. To facilitate description, the steps of method 200 are described with reference to the components of gravimetric sensor 100. However, it will be understood by one of skill in the art from the description herein that different components may be utilized without departing from the spirit and scope of the present invention.

In step 210, liquid is supplied to the channel of a gravimetric sensor. In an exemplary embodiment, a small sample of the liquid to be tested is supplied to nanochannel 150 of gravimetric sensor 100. The liquid may be supplied by conventional means, such as a micropipette or a syringe pump. As set forth above, sensor 100 comprises a piezoelectric resonator 120 having a surface 122 that defines at least a portion of nanochannel 150. Sensor 100 further comprises an encapsulating layer 140 formed on the surface 122 of resonator 120. Encapsulating layer 140 also defines a portion of nanochannel 150 within encapsulating layer 140.

In step 220, the piezoelectric resonator is operated. In an exemplary embodiment, piezoelectric resonator 120 is operated. A voltage differential is applied across piezoelectric material layer 124 using upper electrode 126 and lower electrode 128. Application of the voltage differential causes piezoelectric material layer 124 to vibrate, preferably in a lateral or transverse direction relative to the direction in which nanochannel 150 extends.

In step 230, a change in resonant frequency of the resonator is detected. In an exemplary embodiment, piezoelectric resonator 120 has a resonant frequency before it is exposed to a liquid sample, as explained above. The resonant frequency of resonator 120 is dependent at least in part on the dimensions of the corresponding piezoelectric material layer 124 and the mass of each resonator 120. When surface 122 or functionalization layer 130 of sensor 100 is exposed to the liquid under test, an amount of the analyte will bind to resonator 120. This will change the mass of resonator 120, and thereby, change the resonant frequency of resonator 120. The change in resonant frequency of resonator 120 may be detected during step 220, i.e., when resonator 120 is operated. This change may be detected by conventional means, for example, by monitoring the open-loop impedance of the device, or by connecting the device to a self-sustained oscillator.

The difference in the resonant frequency observed after binding for each resonator 120 may depend on the initial resonant frequency of the resonator 120. For example, a resonator 120 with a low resonant frequency may have a smaller change in resonant frequency after binding, whereas a resonator 120 with a high resonant frequency may have a larger change in resonant frequency after binding. This difference may allow for a broader range of sensitivity to the concentration of a chosen analyte for sensor 100.

In step 240, the presence of the analyte in the liquid is determined. In an exemplary embodiment, as described above, the resonant frequency of resonator 120 is changed when the analyte binds to surface 122 or functionalization layer 130. Accordingly, it may be determined that the analyte is present in the liquid under test when the resonant frequency of resonator 120 changes. Further, the concentration of the analyte in the liquid may be derived from the magnitude of the change in resonant frequency of resonator 120.

Method 200 is not limited to the above steps, but may include additional or alternative steps, as would be understood by one of ordinary skill in the art from the description herein.

For example, it may be desirable to determine the density of the liquid under test using sensor 100. Accordingly, method 200 may include the step of determining the density of the liquid under test. Like the presence of the analyte, the density may be determined based on the change in resonant frequency of resonator 120. The change in resonant frequency is dependent on the change in mass of sensor 100 when liquid is received by sensor 100. Further, the volume of liquid in sensor 100 may be predetermined based on the volume of nanochannel 150. The density of the liquid may therefore be determined using the predetermined volume and the change in mass of the sensor 100 (determined by the change in resonant frequency of resonator 120).

FIGS. 3A-3I are diagrams illustrating an exemplary method 300 for fabricating a gravimetric sensor in accordance with an aspect of the invention. Method 300 may be used to fabricate a gravimetric sensor that detects the amount of a desired analyte in a liquid. As a general overview, method 300 comprises forming a piezoelectric resonator, forming a sacrificial layer, forming an encapsulating layer, and etching the sacrificial layer. Additional details of method 300 are provided herein. To facilitate description, the steps of method 300 are described with reference to the components of gravimetric sensor 100. However, it will be understood by one of skill in the art from the description herein that different components may be utilized without departing from the spirit and scope of the present invention.

Figure 3A:
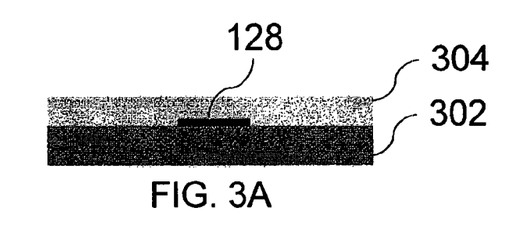
FIGS. 3A-3I are diagrams illustrating an exemplary method for fabricating a gravimetric sensor in accordance with aspects of the present invention.
Figure 3B:
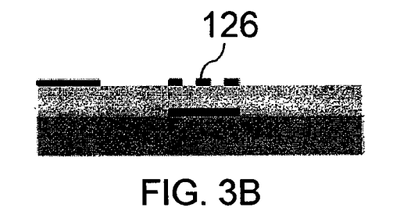
Figure 3C:
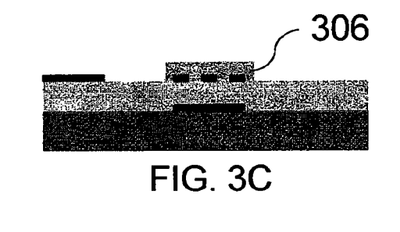
Figure 3D:
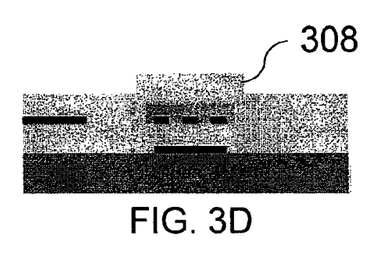
Figure 3E:
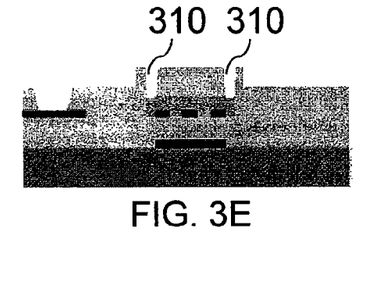

First, a piezoelectric resonator is formed. As shown in FIG. 3A, lower electrode 128 of resonator 120 is formed on a silicon substrate 302. Lower electrode 128 may be formed, for example, by sputter deposition, and may be patterned using optical lithography. As further shown in FIG. 3A, a layer of piezoelectric material 304 is formed overtop substrate 302 and lower electrode 128. Layer of piezoelectric material 304 may be formed, for example, by sputter deposition. As shown in FIG. 3B, upper electrode 126 of resonator 120 is deposited on layer of piezoelectric material 304. Upper electrode 126 may be deposited, for example, by evaporation, and patterned by a lift-off process. In an exemplary embodiment, upper and lower electrodes 126 and 128 are formed from platinum, and are 50 nm thick, and layer of piezoelectric material 304 is formed from aluminum nitride, and is approximately 500 nm thick. To complete the formation of piezoelectric resonator 120, as shown in FIG. 3H, layer of piezoelectric material 304 is etched to free it from the surrounding piezoelectric material, and to define the size of piezoelectric material layer 124.

Prior to the next step, a very thin film (~15 nm) of silicon dioxide ($SiO_2$) may be deposited on the device top surface of layer of upper electrode 126 to enhance the adhesion between upper electrode 126 and the sacrificial layer. This thin film may be deposited, for example, by plasma-enhanced chemical vapor deposition (PECVD).

Next, a sacrificial layer is formed. As shown in FIG. 3C, a sacrificial layer 306 is formed on the upper surfaces of layer of piezoelectric material 304 and upper electrode 126. Sacrificial layer 306 may be formed, for example, by an evaporation process, and patterned through reactive ion etching in $SF_6$ chemistry to define the eventual shape of the nanochannel 150. In an exemplary embodiment, sacrificial layer 306 is formed from amorphous silicon (a-Si), and is approximately 280 nm thick.

Next, an encapsulating layer is formed over the sacrificial layer. As shown in FIG. 3D, another layer of piezoelectric material 308 is formed overtop sacrificial layer 306. Layer of piezoelectric material 308 may also be formed by sputter deposition. In an exemplary embodiment, layer of piezoelectric material 308 is formed from aluminum nitride, and is approximately 600 nm thick. To complete the formation of encapsulating layer 140, as shown in FIG. 3H, layer of piezoelectric material 308 is etched to free it from the surrounding piezoelectric material, and to define the size of encapsulating layer 140.

Next, the sacrificial layer is removed by etching. As shown in FIG. 3E, etch holes 310 are formed in layer of piezoelectric material 308, above the peripheral portion of sacrificial layer 306. Etch holes 310 are also formed at either end (along the length) of sacrificial layer 306, to define the inlet/outlet openings of nanochannel 150. Etch holes 310 may be formed, for example, by inductively coupled plasma (ICP) dry etching. The etch holes 310 formed at the ends of sacrificial layer 306 may be approximately 100 μm by 100 μm in size, and the etch holes formed periodically along the length of sacrificial layer 306 may be 5 μm by 10 μm in size.

Figure 3F:
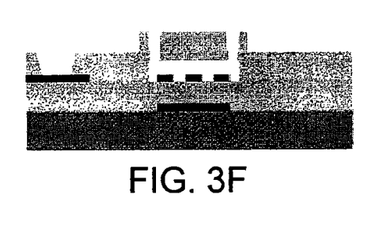
Figure 3G:
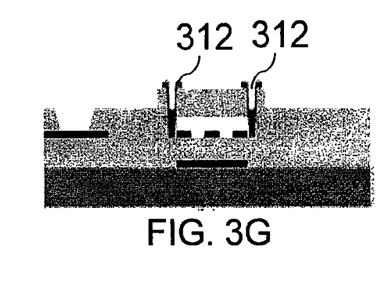
Figure 3H:
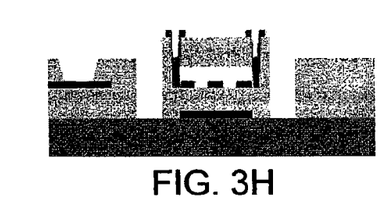

After the formation of etch holes 310, as shown in FIG. 3F, sacrificial layer 306 is etched to remove it. Sacrificial layer 306 may be etched, for example, by dry etching of the sacrificial layer 306 in $XeF_2$ chemistry. After etching, as shown in FIG. 3G, etch holes 310 are sealed. Etch holes 310 may be sealed, for example, with a 500 nm thick $SiO_2$ layer 312 deposited by PECVD. By sealing etch holes 310, nanochannel 150 is formed between layers of piezoelectric material 304 and 308 (which become piezoelectric material layer 124 and encapsulating layer 140, respectively, in FIG. 3H). The shape and size of nanochannel 150 substantially corresponds to the shape and size of sacrificial layer 306 prior to etching.

Figure 3I:
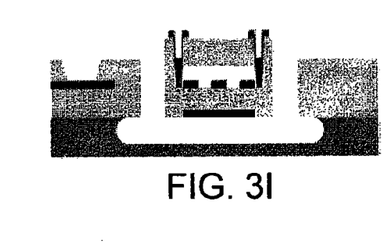

Then, as shown in FIG. 3I, substrate 302 is etched to free resonator 120 from substrate 302. Substrate 302 may be etched so as to form resonator 120 having a cantilevered shape, as set forth above.

EXAMPLE OF THE INVENTION

Figure 4:
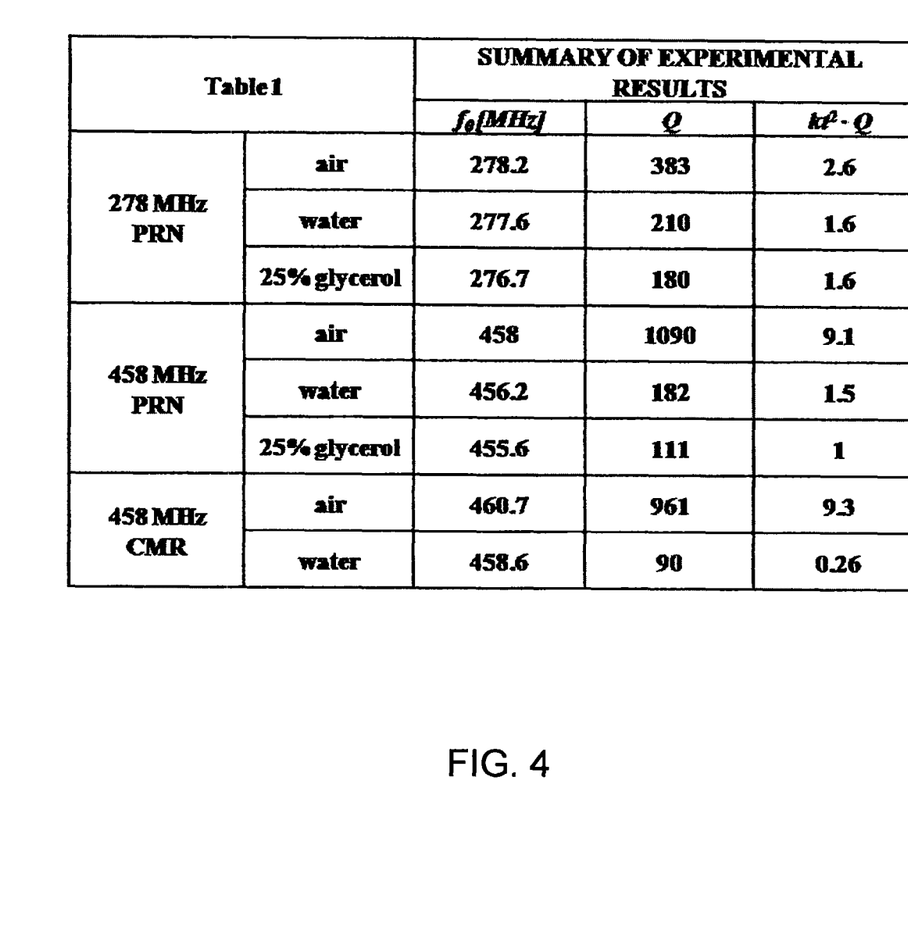
FIG. 4 is a chart illustrating experimental results for an example gravimetric sensor.

Method 300 may be usable to form the following gravimetric sensor, the details of which are set forth as an example for the purposes of illustration. The example gravimetric sensor includes an aluminum nitride piezoelectric resonator incorporating a resonant nanochannel for bio-sensing applications in a liquid environment. The device has a resonant frequency at 278 MHz and 458 MHz. The device shows an unchanged value of the electromechanical coupling, $k_t^2$ (about 0.8%), whether the channel is filled with air or water, and a quality factor, Q, in liquid of approximately 170. The value of $k_t^2$ and Q are in excess of similar values recorded for conventional devices submerged in water. Experimental results for the above sensor are shown by comparison to a conventional contour-mode resonator sensor (CMR) in FIG. 4.

The example sensor formed by method 300 is a contour-mode piezoelectric resonator, and therefore, the electric energy (necessary for actuation of the resonator) is confined within the piezoelectric body of the device, thereby minimizing energy leak into the fluid. The beneficial effect that the above-described resonant nanochannel has on the confinement of electrical energy in the resonant device, and consequently on its electromechanical coupling coefficient, may be confirmed by 2D electrostatic Finite Element Method (FEM) analysis performed using a COMSOL Multiphysics 3.5—Electrostatic AC/DC Module. The presence of fluid (set to be water in the analysis) is such that most of the electrical energy is confined in the fluid rather than the resonator when a CMR is used. When instead the inventive gravimetric sensor is employed, most of the electrical energy is effectively stored in the piezoelectric material (active) layer of the device, rather than the liquid media.

Figure 5:
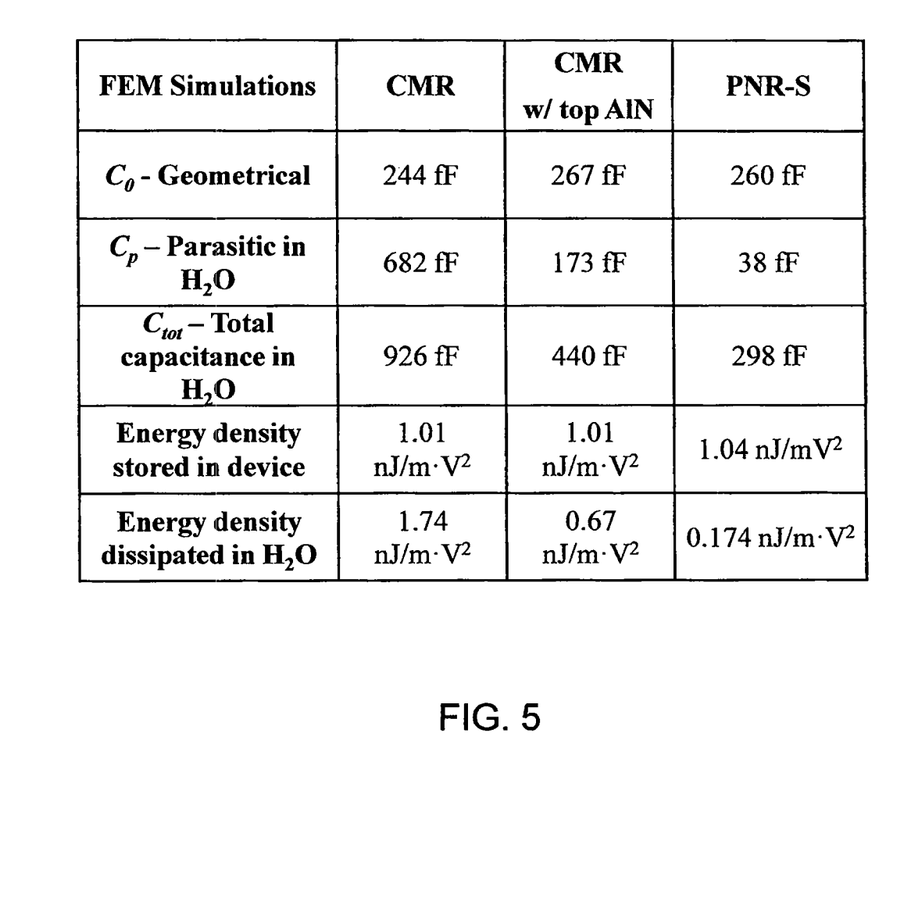
FIG. 5 is another chart illustrating experimental results for the example gravimetric sensor.

This beneficial effect on the device electrical performance can be further seen as a reduction in the parasitic capacitance introduced by the liquid media. In fact, in the conventional CMR-S, the presence of water introduces a large parasitic capacitance, $C_p$ (~680 fF), in parallel to the device geometrical capacitance, $C_0$, which negatively affects the $k_t^2$ of the device ($k_t^2 \propto C_m/C_0$). However, as shown in FIG. 5, in the exemplary gravimetric sensor described herein, the value of such parasitic parallel capacitance, $C_p$, is significantly reduced ($C_p$~38 fF) and negligible if compared to the device capacitance, $C_0$.

The above-described exemplary devices and methods provide advantages over conventional gravimetric sensors, as set forth below.

The disclosed sensor achieves high frequency of operation, reduced viscous damping, improved transduction efficiency and effective delivery of the bio-sample solely on the active sensing surface of the device. By transforming the resonant body of the piezoelectric contour-mode resonator into a laterally vibrating nanochannel, the thickness of the viscous layer as well as the total amount of liquid in contact with the resonator surface may be reduced. Therefore, the new device achieves advantages in the figure of merit ($k_t^2$–Q, product of the electromechanical coupling and resonator Q) with respect to conventional sensors and results in an unchanged $k_t^2$ (approximately 0.8%) with respect to the measurement in air and a Q in fluid of approximately 170. Furthermore, the novel layout permits the delivery of the fluid solely and in close proximity of the sensing surface, therefore resulting in a greatly improved device-sample interaction.

Although the invention is illustrated and described herein with reference to specific embodiments, the invention is not intended to be limited to the details shown. Rather, various modifications may be made in the details within the scope and range of equivalents of the claims and without departing from the invention.

What is claimed:
1. A gravimetric sensor comprising:
   a piezoelectric resonator having a surface; and
   an encapsulating layer formed on the surface of the resonator, the encapsulating layer defining a channel between the surface of the resonator and the encapsulating layer on the surface of the resonator.

2. The sensor of claim 1, wherein
the channel is defined such that an entire length of the channel vibrates with the resonator when the resonator is operated.

3. The sensor of claim 1, wherein
the resonator comprises a first layer of aluminum nitride; and
the encapsulating layer comprises a second layer of aluminum nitride.

4. The sensor of claim 1, further comprising:
a functionalization layer affixed to the surface of the piezoelectric resonator, at least a portion of the functionalization layer positioned within the channel.

5. The sensor of claim 4, wherein
the functionalization layer comprises gold.

6. The sensor of claim 1, wherein
the resonator has a cantilevered shape having a length; and
the channel extends in a direction along the length of the resonator.

7. The sensor of claim 1, wherein
the channel has a volume of less than approximately 50 pL.

8. The sensor of claim 1, wherein
the encapsulating layer covers at least a portion of the surface of the piezoelectric resonator.

9. A method for fabricating a gravimetric sensor comprising:
forming a piezoelectric resonator;
forming a sacrificial layer on a surface of the piezoelectric resonator;
forming an encapsulating layer over the sacrificial layer on the resonator; and
etching the sacrificial layer to remove the sacrificial layer and form a channel between the surface of the resonator and the encapsulating layer on the surface of the resonator.

10. The method of claim 9, wherein the etching step comprises:
forming etch holes at a peripheral portion of the sacrificial layer;
etching the sacrificial layer; and
sealing the etch holes.

11. A method of using a gravimetric sensor to detect an analyte in a liquid, the method comprising the steps of:
supplying the liquid to a channel of the gravimetric sensor, the gravimetric sensor comprising a piezoelectric resonator having a surface and an encapsulating layer formed on the surface of the resonator, the encapsulating layer defining the channel between the surface of the resonator and the encapsulating layer on the surface of the resonator;
operating the piezoelectric resonator;
detecting a change in a resonant frequency of the resonator; and
determining a presence of the analyte in the liquid from the change in resonant frequency of the resonator.

12. The method of claim 11, further comprising the step of determining a density of the liquid from the change in resonant frequency of the resonator.

* * * * *